(12) United States Patent
Kalnes

(10) Patent No.: US 8,686,198 B2
(45) Date of Patent: Apr. 1, 2014

(54) INTEGRATED HYDROLYSIS/HYDROPROCESSING PROCESS FOR CONVERTING FEEDSTOCKS CONTAINING RENEWABLE GLYCERIDES TO PARAFFINS AND POLYOLS

(75) Inventor: Tom N. Kalnes, LaGrange, IL (US)

(73) Assignee: UOP LLC, Des Plaines, IL (US)

( * ) Notice: Subject to any disclaimer, the term of this patent is extended or adjusted under 35 U.S.C. 154(b) by 127 days.

(21) Appl. No.: 13/475,016

(22) Filed: May 18, 2012

(65) Prior Publication Data

US 2013/0310613 A1    Nov. 21, 2013

(51) Int. Cl.
*C07C 27/04*    (2006.01)

(52) U.S. Cl.
USPC ........................................................ 568/864

(58) Field of Classification Search
USPC ........................................................ 568/864
See application file for complete search history.

(56) References Cited

U.S. PATENT DOCUMENTS

| | | |
|---|---|---|
| 7,619,124 B2 | 11/2009 | Miller et al. |
| 7,691,159 B2 | 4/2010 | Li |
| 7,816,570 B2 | 10/2010 | Roberts, IV et al. |
| 8,012,724 B2 | 9/2011 | Holm et al. |
| 8,105,398 B2 | 1/2012 | Morgan |
| 2007/0105204 A1 | 5/2007 | Bao et al. |
| 2010/0050502 A1 | 3/2010 | Wu et al. |
| 2010/0146847 A1 | 6/2010 | Stevens et al. |
| 2010/0186289 A1 | 7/2010 | Bradin et al. |
| 2010/0191008 A1 | 7/2010 | Olson |
| 2011/0092725 A1 | 4/2011 | Jones |
| 2011/0105813 A1 | 5/2011 | Roberts, IV et al. |
| 2011/0107656 A1 | 5/2011 | Miller |
| 2011/0196179 A1 | 8/2011 | Bradin |
| 2011/0250658 A1 | 10/2011 | Franklin et al. |
| 2011/0277376 A1 | 11/2011 | Bloom et al. |
| 2011/0287503 A1 | 11/2011 | Lupton et al. |
| 2011/0294174 A1 | 12/2011 | Franklin et al. |
| 2012/0053357 A1 | 3/2012 | Kale |

FOREIGN PATENT DOCUMENTS

| | | |
|---|---|---|
| WO | WO 2008/012244 A1 | 1/2008 |
| WO | WO2009/037488 A2 | 3/2009 |
| WO | WO 2011/018802 A1 | 2/2011 |

OTHER PUBLICATIONS

Walenziewski et al., "Hydroprocessing of light gas oil-rape oil mixtures," Fuel Processing Technology 90, (2009), pp. 686-691.

*Primary Examiner* — Elvis O Price

(74) *Attorney, Agent, or Firm* — Maryann Maas

(57) ABSTRACT

An integrated process for producing paraffins and polyols from renewable feedstocks has been developed in which a hydrolysis process is integrated with the hydroprocessing step, producing products suitable for use as transportation fuels. Integration allows the use of common equipment which minimizes cost, raw material consumption, and energy requirements.

20 Claims, 3 Drawing Sheets

INTEGRATED HYDROLYSIS/HYDROPROCESSING PROCESS FOR CONVERTING FEEDSTOCKS CONTAINING RENEWABLE GLYCERIDES TO PARAFFINS AND POLYOLS

FIELD OF THE INVENTION

This invention relates generally to a process for producing paraffins useful as transportation fuel and polyols from renewable feedstocks such as the glycerides and free fatty acids found in materials such as plant oils, animal oils, animal fats, and greases. The process involves integrating a hydrolysis step with two hydroprocessing steps.

BACKGROUND OF THE INVENTION

As the demand for fuels such as aviation fuel and chemicals such as propylene glycol increase worldwide, there is increasing interest in sources other than petroleum crude oil for producing the fuel or chemical. One source is renewable feedstocks including, but not limited to, plant oils such as corn, jatropha, camelina, rapeseed, canola, soybean and algal oils, animal fats such as tallow, fish oils, and various waste streams such as yellow and brown greases and oily streams recovered from sewage sludge. The common feature of these feedstocks is that they are composed of mono- di- and tri-glycerides, and free fatty acids (FAAs). Most of the glycerides in the renewable feed stocks will be triglycerides, but some may be monoglycerides or diglycerides. The monoglycerides and diglycerides can be processed along with the triglycerides.

There are reports disclosing the production of hydrocarbons from oils. For example, U.S. Pat. No. 4,300,009 discloses the use of crystalline aluminosilicate zeolites to convert plant oils (e.g., corn oil) to hydrocarbons (e.g., gasoline), and chemicals (e.g., para-xylene). U.S. Pat. No. 4,992,605 discloses the production of hydrocarbon products in the diesel boiling range by hydroprocessing vegetable oils such as canola or sunflower oil. Finally, US 2004/0230085 A1 discloses a process for treating a hydrocarbon component of biological origin by hydrodeoxygenation followed by isomerization.

However, existing processes for converting fats and oils to biodiesel and glycerol have been criticized because of the quality of the diesel produced and the oversupply of glycerol. In addition, current processes for producing transportation fuel from renewable feedstocks have been criticized because of concerns over the high investment cost and operating costs.

SUMMARY OF THE INVENTION

One aspect of the invention is an integrated process for producing paraffins and polyols from a glyceride containing renewable feedstock. In one embodiment, the process includes reacting the glyceride containing renewable feedstock with water in a first reaction zone to produce an effluent stream comprising free fatty acids, glycerol, and water. The free fatty acids are separated from the glycerol and water to produce a free fatty acid stream substantially free of glycerol, water, and metals and a glycerol stream substantially free of free fatty acids. The free fatty acid stream substantially free of glycerol, water, and metals is reacted with hydrogen from a hydrogen source in a second reaction zone in the presence of a hydroprocessing catalyst under hydroprocessing conditions thereby hydrodeoxygenating the free fatty acid stream substantially free of glycerol, water, and metals to produce a reaction product comprising n-paraffins and water, and the n-paraffin reaction product is then recovered. The glycerol stream substantially free of free fatty acids is reacted with hydrogen from the hydrogen source in a third reaction zone under selective hydrogenation conditions to produce a reaction product comprising polyols, and the polyols reaction product is recovered.

DETAILED DESCRIPTION OF THE INVENTION

Figure 1:
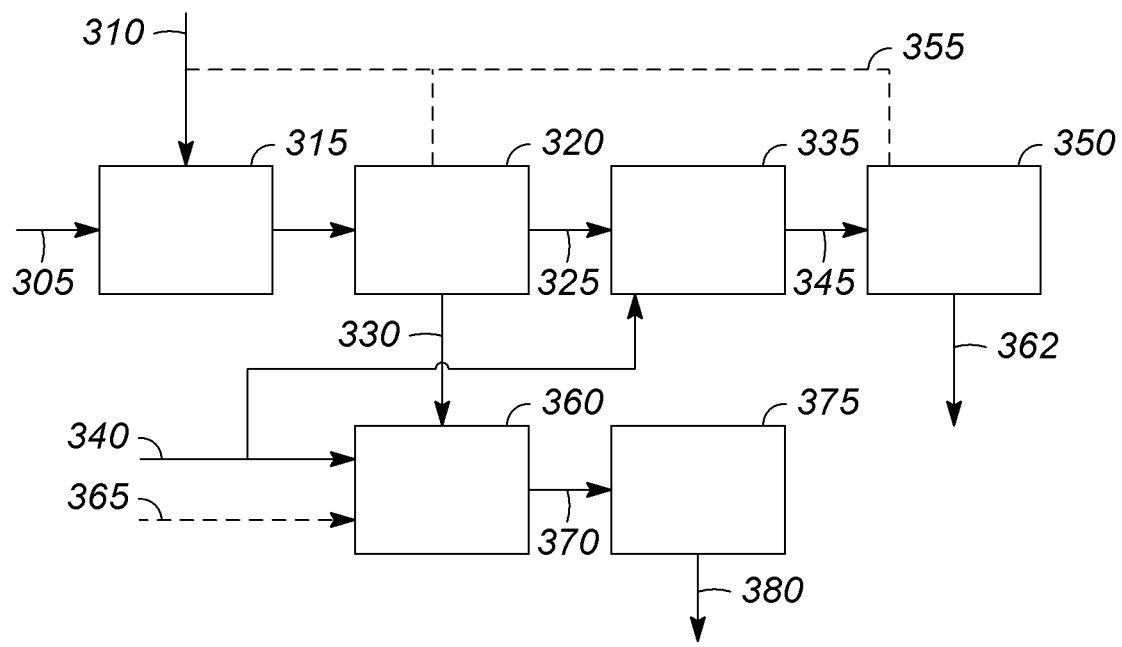
FIG. 1 is a schematic of one embodiment of an integrated hydrolysis/hydroprocessing process.

The present invention relates to a process for producing a paraffin stream having boiling points in the diesel, naphtha, and aviation fuel range from renewable feedstocks originating from plants or animals other than petroleum feedstocks. By integrating hydrolysis and hydroprocessing, the same fats and oils used in the prior art biodiesel processes can be converted to paraffins suitable for use as transportation fuels. The process produces a more valuable co-product, polyol instead of glycerol. By integrating the hydrolysis and hydroprocessing steps, common equipment can be used to minimize investment cost, raw material consumption, and energy requirements. The integrated process also allows the use of renewable feedstocks containing high levels of metals without damaging the hydroprocessing catalysts. In one embodiment, the process uses less hydrogen than the previous process.

A process was developed to produce green diesel from natural oils and fats. The process involved deoxygenating renewable feedstocks with carbon chain lengths in the diesel range to produce n-paraffins with both the same number of carbons as the fatty acid chain, or one carbon less if the oxygen was removed by decarboxylation or decarbonylation. In an optional second stage of the process, a portion of the n-paraffins is selectively isomerized to improve the cold properties of the resulting diesel. The process uses a significant amount of hydrogen to support the chemistry of converting the triglycerides to diesel fuel and propane.

An alternative method of producing renewable hydrocarbons from lower cost or more sustainable feedstocks would be desirable, both from an economic standpoint (i.e., lower raw material cost and more valuable co-products) and from an environmental standpoint (i.e., less green house gas emissions). In addition, reduced hydrogen consumption would also be desirable.

Moreover, renewable feedstocks may contain a variety of impurities. For example, the renewable feedstocks may contain contaminants such as alkali metals, e.g. sodium and potassium, phosphorous, gums, and water. The renewable feedstocks typically may contain from about 10 ppm (wt) to over 5000 ppm (wt) of total metals. By "total metals" we mean the combined amount of Si, Fe, Al, K, Na, Mg, Cu, Ca, Ti, Mn, Zn and P in the feedstock. These metals can be deleterious to the hydrodeoxygenation catalyst. Therefore, it is desirable to remove at least a portion of the metals before the feed reaches the hydrodeoxygenation catalyst.

A hydrolysis process can be integrated with the hydroprocessing step, producing a paraffin product suitable for use as a transportation fuel. Integration reduces overall hydrogen consumption, process energy input and fresh water consumption and allows the use of common equipment. Taken together, these differences translate into lower operating costs and/or lower capital investment per unit of paraffin product.

In the hydrolysis step, water is reacted with the glyceride-containing feedstock to produce the corresponding FFA molecules and glycerol by hydrolysis chemistry. The hydrolysis can be thermal or catalytic. The reaction products are separated into a free fatty acid stream substantially free of glycerol, water, and metals, and a glycerol containing stream. After separation, the FFAs are processed as discussed above to obtain a paraffin-rich product suitable for use as a transportation fuel, and the glycerol is converted into polyol. In one embodiment, the net result is a shift from converting the triglycerides to diesel and propane to converting the triglycerides to diesel and propylene glycol while minimizing the overall hydrogen consumption.

By "glyceride-containing feedstock," we mean a stream comprising at least 5 wt % total glycerides by dry weight, or at least 10 wt %, or at least 20 wt %, or at least 30 wt %, or at least 40 wt %, or at least 50 wt %. By "free fatty acid stream substantially free of glycerol, water, and metals" we mean that the stream contains less than about 10 wt % glycerol, or less than about 5 wt % glycerol, or less than about 3 wt % glycerol, or less than about 1 wt % glycerol, or less than about 0.75 wt %, or less than 0.50 wt %. There is less than about 10 wt % water, or less than about 5 wt % water, or less than about 3 wt %, or less than about 1 wt %. The stream has less than about 20 ppm (wt) total metals, or less than about 15 ppm (wt), or less than 10 ppm (wt). The higher amounts of glycerol and water in the free fatty acid stream substantially free of glycerol water and metals are less desirable because the economics are not as favorable; however, in certain situations, they may be acceptable. By "glycerol stream substantially free of free fatty acids," we mean a stream comprising less than 5 wt % of the total amount of fatty acids present in the glyceride-containing feedstock. By "glycerol containing stream," we mean a stream comprising at least 30% (wt) glycerol; it may contain water, and possibly some FFAs.

The hydrolysis step is typically performed at sub-critical conditions. Desirable conditions for the hydrolysis step are less than about 300° C. and less than about 5516 kPa (g) (800 psig), or less than about 250° C. and less than about 3447 kPa (g) (500 psig), or less than about 150° C. and less than about 2068 kPa (g) (300 psig). Critical and near critical conditions (supercritical water is defined as greater than about 374° C. and about 22,063 kPa (g) (3200 psig)) are far less desirable because as conditions approach critical conditions, the water mixture becomes highly corrosive, and the metallurgical requirements become cost prohibitive.

The ratio of water to total lipids in the hydrolysis step is typically greater than the stoichiometric minimum required for complete hydrolysis.

In some embodiments, a hydrolysis catalyst will be needed in order to achieve some desirable operating conditions. Suitable hydrolysis catalysts include, but are not limited to, acidic catalysts. The hydrolysis catalyst can be a solid or a liquid. Suitable liquid catalysts include, but are not limited to, ionic liquids. Suitable solid catalysts include, but are not limited to, solid acid catalysts. The solid catalyst can be supported on a material that is stable at hydrolysis conditions. Examples of catalyst support materials which are stable over part of the range of operating conditions include, but are not limited to, amorphous carbon, activated carbon, titanium oxide and zirconium oxide.

The hydrolysis step can optionally be preceded by a feed pretreatment step to remove contaminants such as metals, nitrogen, sulfur and other inorganic species. Feed pretreatment is discussed further below. The pretreatment can be designed and operated to retain at least about 80%, or at least about 90% of the total lipid and free fatty acids present in the feedstock in the hydrolysis reactor feed. By "total lipids," we mean any of a group of organic compounds, including the fats, oils, waxes, sterols, and glycerides, that are insoluble in water but soluble in organic solvents, and are oily to the touch.

Although conventional processes utilize a dry feedstock, the present process does not require the renewable feedstock to be dry. The feedstock can contain more than about 5% moisture, and in some cases, the feedstock moisture content can be as much as five times the total lipid plus free acid concentration.

Feedstocks include all renewable sources of lipids and free fatty acids. Special emphasis is placed on low cost waste-derived feedstocks, such as brown grease, yellow grease, inedible tallow, used cooking oils, and mixtures containing these materials. The feedstock total lipid to fatty acid ratio can be from 0.05 to 0.995 on a molar basis depending on feedstock source. Other feedstocks include crude and refined vegetable oils with special emphasis on lower cost crude vegetable oils unsuitable for direct use as feedstock for transesterification or hydroconversion processes due to the presence of alkali metals, gums and phospholipids. A desirable feedstock is one containing algal lipids, and particularly an algal feedstock enriched in total lipids plus free fatty acids by pretreatment to remove proteins and cellulose (e.g., mild acid hydrolysis). Suitable feedstocks are discussed in more detail below.

Typically, the hydrolysis step is operated to convert at least about 80%, or at least about 90%, or at least about 95% of the total lipids present in the feedstock (including polar lipids) to free fatty acids. Typically, at least about 10% of the polar lipids are converted to FFA by hydrolysis.

The hydrolysis step can be continuous in nature and can operate at steady state conditions (i.e., constant temperature, pressure, and flow), if desired.

In one embodiment, the ratio of water to total lipids is greater than the stoichiometric requirement, or in excess of three (3) times the stoichiometric requirement needed for hydrolysis.

The recovery of FFA from the hydrolysis reactor involves a series of steps including, but not limited to, one or more of the following: hot depressurization, cyclonic vapor-liquid separators, liquid-liquid separators, multi-effect evaporators, steam distillation, vacuum distillation, reactive distillation, liquid extraction, adsorption, filtration, membrane separation, absorption, and ion exchange to produce a FFA stream of adequate purity to be directly fed to a fixed bed catalytic hydrodeoxygenation reactor for conversion of the FFA to hydrocarbon fuel. Desirably, the stream entering the hydrodeoxygenation reactor should include less than about 20 ppm (wt) total metals, less than about 5% by weight total glycerol, and less than about 5% by weight total water.

Typically, at least about 90% of the FFA present in the hydrolysis reactor is recovered in the FFA recovery section of the process.

The deoxygenation zone can be catalytic or thermal, selective or non-selective. In one embodiment, selective catalytic hydrodeoxygenation can be used to maximize the yield of paraffins suitable for use as transportation fuels.

Selective catalytic hydrodeoxygenation provides several benefits. Less than about 10% of the FFA carbon is lost to $CO/CO_2$ by decarboxylation and decarbonylation reactions. The $H_2$ partial pressure at the hydrodeoxygenation reactor outlet is greater than about 3447 kPa (500 psia), or more than about 5516 kPa (800 psia). The hydrogen supplied to the reactor is generally at least three times the stoichiometric requirement for 100% conversion of feedstock organic oxygen to water. Typically, more than about 80% of the oxygen in the free fatty acid stream substantially free of glycerol, water, and metals is converted to water. Generally, the resultant hydrocarbon is distillate (diesel plus kerosene) with an aromatic content of less than about 1% and a paraffin content of more than about 90%.

The hydrodeoxygenation zone effluent can be routed to a selective isomerization zone for improving distillate cold flow properties while minimizing cracking to naphtha and lighter hydrocarbons, if desired.

Water produced in the hydrodeoxygenation zone can be recycled as at least a portion of the make-up water to the hydrolysis step (see FIG. 1), if desired.

In some embodiments, at least a portion of the hydrogen supplied to the hydrogenation reactor is excess hydrogen recovered from the reactor product and recycled to the reactor to achieve the hydrogen partial pressure targets discussed above.

The recovery of glycerol from the hydrolysis reactor involves a series of steps such as those described above with respect to the FFA stream to produce a glycerol stream of adequate purity for the selective hydrogenation step. The selective hydrogenation step typically uses a noble metal catalyst. The process typically operates at a temperature in the range of about 150° C. to about 250° C., a pressure in the range of about 3447 kPa (g) (500 psig) to about 13790 kPa (g) (2000 psig), and a weight hourly space velocity (WHSV) of about 0.2 to about 2 $hr^{-1}$. Small amounts (generally in the range of about 1 wt % to about 3 wt %) of alkali (NaOH) are injected into the reaction zone to improve the activity and/or the selectivity.

In one embodiment as shown in FIG. 1, a pretreated renewable glyceride-rich feedstock 305 and water 310 enter a hydrolysis zone 315. The glycerides are hydrolyzed to FFAs and glycerol. The FFAs and glycerol hydrolysis products enter a separation zone 320. The FFAs and glycerol are separated into a free fatty acid stream substantially free of glycerol, water, and metals 325 and a glycerol containing stream 330. The separation zone 320 is described in more detail below.

The free fatty acid stream substantially free of glycerol, water, and metals 325 is sent to the hydroprocessing zone 335 where the FFAs are reacted with hydrogen from hydrogen source 340 to produce a paraffin product useful as a transportation fuel 345 which is sent to recovery zone 350 where the n-paraffin product 362 is recovered.

Optionally, recycle water 355 from the separation zone 320 and/or the paraffin recovery zone 350 can be combined with make-up water to provide at least a portion of the water stream 310 for the hydrolysis zone 315.

The glycerol containing stream 330 is sent to selective hydrogenation zone 360, where it is reacted with hydrogen from hydrogen source 340 in the presence of a hydrogenation catalyst and small amounts of alkali 365. The polyol product 370 is then recovered in polyol recovery zone 375 as polyol product 385.

Figure 2:
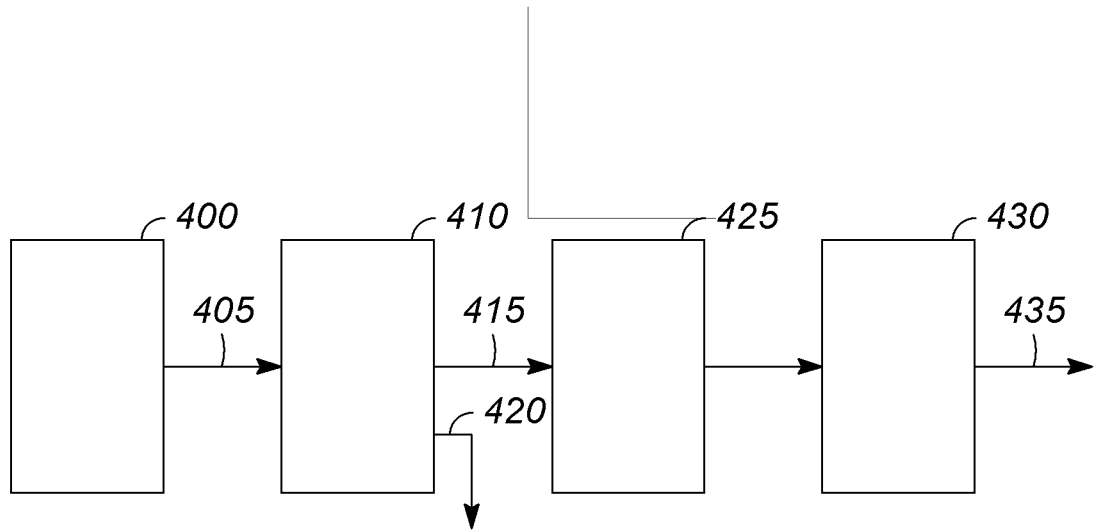
FIG. 2 is a schematic of one embodiment of a separation step.

One embodiment of a process for separating the hydrolysis products into the free fatty acid stream substantially free of glycerol, water, and metals and the glycerol-containing stream is illustrated in FIG. 2. The effluent 405 from the hydrolysis zone 400 enters extraction column 410. The extraction column 410 separates the product into a free fatty acid enriched stream 415 and a glycerol-containing stream 420. The free fatty acid enriched stream 415 is optionally sent to one or more purification devices 425, 430 to remove water, glycerol, and metals producing the free fatty acid stream substantially free of glycerol, water, and metals 435. The free fatty acid stream substantially free of glycerol, water, and metals 435 is sent to the hydroprocessing zone where it is reacted with hydrogen in the presence of a catalyst to hydrodeoxygenate it, producing n-paraffins and water.

Similar processes and equipment can be used to separate and purify the glycerol containing stream to the glycerol stream substantially free of free fatty acids.

The operating conditions and catalyst types can be adjusted for the hydrolysis and hydrodeoxygenation processes to control the amount of organic oxygen in the feed which is converted to $CO_2$ instead of water, if desired.

Suitable renewable feedstocks include those originating from plants or animals. Some of these feedstocks are known as renewable fats and oils. The term renewable feedstock is meant to include feedstocks other than those obtained from petroleum crude oil. The renewable feedstocks that can be used in the present invention include any of those which comprise glycerides and FFA. Most of the glycerides will be triglycerides, but monoglycerides and diglycerides may be present and processed as well. Examples of these feedstocks include, but are not limited to, canola oil, corn oil, soy oils, rapeseed oil, soybean oil, colza oil, tall oil, sunflower oil, hempseed oil, olive oil, linseed oil, coconut oil, castor oil, peanut oil, pennycress oil, palm oil, carinata oil, jojoba oil, mustard oil, cottonseed oil, jatropha oil, tallow, yellow and brown greases, lard, train oil, fats in milk, fish oil, algal oil, sewage sludge, and the like. Additional examples of renewable feedstocks include non-edible vegetable oils from the group comprising Jatropha curcas (Ratanjoy, Wild Castor, Jangli Erandi), Madhuca indica (Mohuwa), Pongamia pinnata (Karanji Honge), and Azadiracta indicia (Neem). The triglycerides and FFAs of the typical vegetable or animal fat contain aliphatic hydrocarbon chains in their structure which have about 8 to about 24 carbon atoms, with a majority of the fats and oils containing high concentrations of fatty acids with 16 and 18 carbon atoms. Mixtures or co-feeds of renewable feedstocks and petroleum derived hydrocarbons may also be used as the feedstock. Other feedstock components which may be used, especially as a co-feed component in combination with the above listed feedstocks, include spent motor oils and industrial lubricants, used paraffin waxes, liquids derived from the gasification of coal, biomass, or natural gas followed by a downstream liquefaction step such as Fischer-Tropsch technology, liquids derived from depolymerization, thermal or chemical, of waste plastics such as polypropylene, high density polyethylene, and low density polyethylene; and other synthetic oils generated as byproducts from petrochemical and chemical processes. Mixtures of the above feedstocks may also be used as co-feed components. In some applications, an advantage of using a co-feed component is the transformation of what may have been considered to be a waste product from a petroleum based or other process into a valuable co-feed component to the current process.

Algae are one type of biomass that is of particular interest because they are one of the fastest growing plants on the planet, therefore offering one of the highest yields per unit area. Algae also do not need arable land, and can be grown with impaired water. Algae have been used as a feedstock to produce biofuel using various methods. Algae contain neutral lipids (triacylglycerols (TAGs)), glycolipids found in algal chloroplast membranes (e.g., monogalactosyldiacylglycerols and digalactosyldiacylglycerols), and polar lipids of the algal plasma membranes, primarily phospholipids (e.g., phosphatidylcholine). The glycolipids and other polar lipids represent a significant portion of the total lipids in the algae. Conventional production methods of making biofuel from algae use only a fraction (the neutral lipids) of the total available lipid material in the algae leaving a large percentage of "residual algal biomass" remaining after the TAG lipids have been extracted to form a neutral oil extract. Conventional methods are incapable of converting the glycolipids and other polar lipids in the algae into biofuel. These lipids cannot be extracted from algal biomass by conventional methods, and thus, cannot be recovered by downstream hydrolysis. Therefore, conventional methods produce only a small fraction of the energy that can potentially be obtained from the algae.

US Publication No. 2011/0287503, which is incorporated herein by reference, describes a method of making hydrocarbons from algal biomass. The algal biomass is formed from algae. The term "algae" as used herein refers to any organisms with chlorophyll and a thallus not differentiated into roots, steams and leaves, and encompasses prokaryotic organisms such as CYANOBACTERIA (Blue-green algae) and eukaryotic organisms that are photoautotrophic or photoauxotropic. The term "algae" includes macroalgae (commonly known as seaweed) and microalgae. The algal biomass may also comprise dried algae. Algae may include any species or strain in the following taxonomic groups: BACILLARIOPHYTA (diatoms), CHAROPHYTA (stoneworts), CHLOROPHYTA (green algae), CHRYSOPHYTA (golden algae), DINOPHYTA (dinoflagellates), HAEOPHYTA (brown algae), RHODOPHYTA (red algae), CYANOPHYTA, PROCHLOROPHYTA, GLAUCOPHYTA, CRYPTOPHYTA, PRYMNESIOPHYTA, XANTHOPHYTA, RHAPHIDOPHYTA, PHAEOPHYTA, and EUSTIGMATOPHYTE (algae). Examples of suitable algae are described in Section 5.2 of U.S. Publication No. 2010/0050502, which section is incorporated herein by reference. One example of suitable algae is NANOCHLOROPSIS (marine algae).

Algal biomass may be provided by harvesting algae from a source such as a bioreactor, aquaculture pond, waste water, lake, pond, river, sea, etc. The algae may be, for example, a naturally occurring species, a genetically selected strain, a genetically manipulated strain, a transgenic strain, a synthetic algae, or combinations thereof. Algae grow as a dilute suspension. The algae feedstock can be either wet or dry. Using a wet feedstock is desirable because it is less expensive than dry feedstock. In one embodiment, to obtain a dry feedstock, the harvested algae can be dewatered, for example in a concentrator. The concentrator concentrates the algae producing the whole algal biomass. The whole algal biomass comprises a concentrated algal paste of about 4% to about 12% solids by weight. The term "about", as used hereinafter, unless otherwise indicated, refers to a value that is no more than 20% above or below the value being modified by the term. The concentrated algal paste is in the form of slurry with a paste-like consistency, able to be pumped from the concentrator into a reactor. Any one or more known methods for dewatering the algae in the concentrator can be used, including but not limited to, sedimentation, filtration, centrifugation, flocculation, froth floatation, and/or semipermeable membranes. The whole algal biomass is also commercially available from sources such as algal cultivators, Solix Biofuels Inc., Fort Collins, Colo. (USA) and Cyanotech Corp., Hawaii (USA).

The algae can undergo extraction, although this is not required. To form the residual algal biomass, the whole algal biomass from concentrator is dried in a dryer by evaporation or the like to provide dried concentrated algal paste. The neutral triacyglycerols (TAGs) are then extracted from the dried concentrated algal paste in a neutral lipid extractor by known lipid extraction methods using an organic solvent such as hexane or the like to produce a "neutral oil extract" (also referred to herein as "TAG oil"). The TAG oil produced during the extracting step may be withdrawn from the neutral lipid extractor. A mixture of the organic solvent and TAG oil is provided to an input of an evaporator. The organic solvent is evaporated in the evaporator leaving the TAG oil which can be sent to a downstream process.

"Residual algal biomass" refers to the dried bagasse remaining after the neutral lipids, e.g., triacylycerols (TAGs), are recovered as "TAG oil" by the solvent extraction. The residual algal biomass comprises the polar lipids and the glycolipids, residual protein and carbohydrates, and algal cell debris. The total mass of the bagasse after the solvent extraction of TAG oil is at least 70% of the total algal biomass.

The algal biomass comprised of whole algal biomass from the concentrator, the TAG oil, or combinations thereof, can be introduced as feedstock to the first reactor.

As discussed above, the renewable feedstock can be pretreated before entering the hydrolysis zone to remove contaminants. Suitable pretreatments include, but are not limited to, contacting the glyceride-containing renewable feedstock with one or more of a acid, a base, an extractive material, or an adsorptive material.

One possible pretreatment step involves contacting the renewable feedstock with an ion-exchange resin in a pretreatment zone at pretreatment conditions. In one embodiment, the ion-exchange resin is an acidic ion exchange resin such as Amberlyst™15 and can be used as a bed in a reactor through which the feedstock is flowed, either upflow or downflow.

Another possible method of removing contaminants is a mild acid wash. This is carried out by contacting the feedstock with an acid such as sulfuric, nitric or hydrochloric acid in a reactor. The acid and feedstock can be contacted either in a batch or continuous process. Contacting is done with a dilute acid solution usually at ambient temperature and atmospheric pressure. If the contacting is done in a continuous manner, it is usually done in a counter current manner. Yet another possible means of removing metal contaminants from the feedstock is through the use of guard beds which are well known in the art. These can include alumina guard beds either with or without demetallation catalysts such as nickel or cobalt. Filtration and solvent extraction techniques are other choices which may be employed.

Hydroprocessing such as that described in U.S. Pat. No. 7,638,040 or 8,038,869, for example, each of which is, hereby incorporated by reference, are other pretreatment techniques which may be employed.

The free fatty acid stream substantially free of glycerol, water, and metals from the separation zone flows to the hydroprocessing zone comprising one or more catalyst beds in one or more reactors. In the hydroprocessing zone, the free fatty acid stream substantially free of glycerol, water, and metals is contacted with a hydrogenation or hydrotreating catalyst in the presence of hydrogen at hydrogenation conditions to hydrogenate the reactive components such as olefinic or unsaturated portions of the n-paraffinic chains. Hydrogenation and hydrotreating catalysts are any of those well known in the art such as nickel or nickel/molybdenum dispersed on a high surface area support. Other hydrogenation catalysts include one or more noble metal catalytic elements dispersed on a high surface area support. Non-limiting examples of noble metals include Pt and/or Pd dispersed on gamma-alumina, titanium oxide or activated carbon.

Hydrogenation conditions include a temperature of about 40° C. to about 400° C. and a pressure of about 689 kPa absolute (100 psia) to about 13,790 kPa absolute (2000 psia). Other operating conditions for the hydrogenation zone are well known in the art.

For hydrodeoxygenation, the conditions include a temperature of about 200° C. to about 400° C. and a pressure of about 4137 kPa absolute (600 psia) to about 8274 kPa absolute (1200 psia). The hydrogen partial pressure is typically greater than about 3450 kPa absolute (500 psia). The ratio of $H_2$ to organic oxygen is generally greater than about 5, or greater than about 7, or greater than about 10. Suitable catalysts for hydrodeoxygenation include, but are not limited to, nickel or nickel/molybdenum containing catalysts.

Some of the catalysts enumerated above are also capable of catalyzing decarboxylation, and decarbonylation in addition to hydrodeoxygenation of the feedstock to remove oxygen. Decarboxylation, decarbonylation, and hydrodeoxygenation are collectively referred to as deoxygenation reactions. In some situations, decarboxylation and decarbonylation can be less desirable because of the loss of renewable carbon feedstock to CO and $CO_2$. Decarboxylation conditions include a relatively low pressure of about 689 kPa (100 psia) to about 6895 kPa (1000 psia), a temperature of about 300° C. to about 450° C. and a liquid hourly space velocity of about 0.5 to about 10 $hr^{-1}$. Since hydrogenation is an exothermic reaction, as the feedstock flows through the catalyst bed, the temperature increases and decarboxylation and hydrodeoxygenation will begin to occur. Thus, it is envisioned and is within the scope of this invention that all the reactions can occur simultaneously in one reactor or in one bed.

Alternatively, the conditions can be controlled such that hydrogenation primarily occurs in one bed and decarboxylation and/or hydrodeoxygenation occurs in a second bed. Of course, if only one bed is used, then hydrogenation occurs primarily at the front of the bed, while decarboxylation/hydrodeoxygenation occurs mainly in the middle and bottom of the bed. Finally, desired hydrogenation can be carried out in one reactor, while decarboxylation, decarbonylation, and/or hydrodeoxygenation can be carried out in a separate reactor.

The effluent from the deoxygenation zone is conducted to a hot high pressure hydrogen stripper. The reaction product from the deoxygenation reactions will comprise both a liquid portion and a gaseous portion. The liquid portion comprises a hydrocarbon fraction which is essentially all n-paraffins and having a large concentration of paraffins in the range of about 8 to about 18 carbon atoms. The gaseous portion comprises hydrogen, carbon dioxide, carbon monoxide, water vapor, propane, and perhaps sulfur components, such as hydrogen sulfide or phosphorous components such as phosphine, or nitrogen compounds such as ammonia. One purpose of the hot high pressure hydrogen stripper is selectively to separate at least a portion of the gaseous portion of the effluent from the liquid portion of the effluent.

Failure to remove the water, trace carbon monoxide, ammonia, and carbon dioxide from the effluent may result in poor catalyst performance in the isomerization zone. Water, carbon monoxide, carbon dioxide, and/or hydrogen sulfide are selectively stripped in the hot high pressure hydrogen stripper using hydrogen. The hydrogen used for the stripping may be dry, and free of carbon oxides.

The temperature may be controlled in a limited range to achieve the desired separation and the pressure may be maintained at approximately the same pressure as the two reaction zones to minimize both investment and operating costs. The hot high pressure hydrogen stripper may be operated at conditions ranging from a pressure of about 689 kPa absolute (100 psia) to about 13,790 kPa absolute (2000 psia), and a temperature of about 40° C. to about 350° C. In another embodiment the hot high pressure hydrogen stripper may be operated at conditions ranging from a pressure of about 1379 kPa absolute (200 psia) to about 4826 kPa absolute (700 psia), or about 2413 kPa absolute (350 psia) to about 4882 kPa absolute (650 psia), and a temperature of about 50° C. to about 350° C. The hot high pressure hydrogen stripper may be operated at essentially the same pressure as the reaction zone. By "essentially", it is meant that the operating pressure of the hot high pressure hydrogen stripper is within about 1034 kPa absolute (150 psia) of the operating pressure of the reaction zone. For example, in one embodiment the hot high pressure hydrogen stripper separation zone is no more than about 1034 kPa absolute (150 psia) less than that of the reaction zone.

The effluent from the deoxygenation reaction enters the hot high pressure stripper, and at least a portion of the gaseous components are carried with the hydrogen stripping gas and separated into an overhead stream. The remainder of the deoxygenation zone effluent stream is removed as hot high pressure hydrogen stripper bottoms and contains the liquid hydrocarbon fraction having components such as normal hydrocarbons having from about 8 to about 24 carbon atoms. Different feedstocks will result in different distributions of paraffins. A portion of this liquid hydrocarbon fraction in hot high pressure hydrogen stripper bottoms may be used as the hydrocarbon recycle described below.

Hydrogen may be separated from process effluent(s) and recycled to the hydrogenation and deoxygenation zone, or the amount of hydrogen may be in only slight excess, about 5 to about 25%, of the hydrogen requirements of the hydrogenation and deoxygenation reactions and therefore not recycled. Another refinery unit, such as a hydrocracker, may be used as a source of hydrogen, which potentially eliminates the need for a recycle gas compressor.

In one embodiment, the desired amount of hydrogen is kept in solution at lower pressures by employing a large recycle of hydrocarbon to the deoxygenation reaction zone. Other processes have employed hydrocarbon recycle in order to control the temperature in the reaction zones since the reactions are exothermic reactions. However, the range of recycle to feedstock ratios is not always determined on temperature control requirements. In some cases, it is based upon hydrogen solubility requirements. Hydrogen has a greater solubility in the hydrocarbon product than it does in the feedstock. By utilizing a large hydrocarbon recycle, the solubility of hydrogen in the combined liquid phase in the reaction zone is greatly increased, and higher pressures are not needed to increase the amount of hydrogen in solution. In one embodiment of the invention, the volume ratio of hydrocarbon recycle to feedstock is from about 2:1 to about 8:1, or about 2:1 to about 6:1. In another embodiment, the ratio is in the range of about 3:1 to about 6:1, and in yet another embodiment, the ratio is in the range of about 4:1 to about 5:1.

Although the hydrocarbon fraction separated in the hot high pressure hydrogen stripper is useful as a diesel boiling range fuel, it will have poor cold flow properties because it comprises essentially n-paraffins. The hydrocarbon fraction can be contacted with an isomerization catalyst under isomerization conditions to selectively isomerize at least a portion of the n-paraffins to branched paraffins to improve the cold flow properties. The effluent of the isomerization zone is a branched-paraffin-rich stream. By the term "rich" it is meant that the effluent stream has a greater concentration of branched paraffins than the stream entering the isomerization zone, and can comprises greater than about 15 mass-% branched paraffins. It is envisioned that the isomerization zone effluent may contain greater than about 20, or greater than about 30, or greater than about 40, or greater than about 50, or greater than about 60, or greater than about 70, or greater than about 75, or greater than about 80, or greater than about 90 mass-% branched paraffins.

Isomerization can be carried out in a separate bed of the same reaction zone, i.e., same reactor described above for deoxygenation, or the isomerization can be carried out in a separate reactor. For ease of description, an embodiment with a separate reactor for the isomerization reaction will be described. The hydrogen stripped product of the deoxygenation reaction zone is contacted with hydrogen in the presence of an isomerization catalyst at isomerization conditions to isomerize the normal paraffins to branched paraffins. Only minimal branching is required, enough to overcome the cold-flow problems of the normal paraffins. Because attempting to obtain significant branching runs the risk of undesired cracking, the predominant isomerized product is a mono-branched hydrocarbon.

The isomerization of the paraffinic product can be accomplished in any manner known in the art or by using any suitable catalyst known in the art. One or more beds of catalyst may be used. It is preferred that the isomerization be operated in a co-current mode of operation. Fixed bed, trickle bed down flow or fixed bed liquid filled up-flow modes are both suitable. See also, for example, US 2004/0230085 A1 which is incorporated by reference in its entirety. Suitable catalysts comprise a metal of Group VIII (IUPAC8-10) of the Periodic Table and a support material. Suitable Group VIII metals include platinum and palladium, each of which may be used alone or in combination. The support material may be amorphous or crystalline. Suitable support materials include, but are not limited to, amorphous alumina, titanium oxide, amorphous silica-alumina, ferrierite, ALPO-31, SAPO-11, SAPO-31, SAPO-37, SAPO-41, SM-3, MgAPSO-31, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MgAPSO-11, MgAPSO-31, MgAPSO-41, MgAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite, each of which may be used alone or in combination. ALPO-31 is described in U.S. Pat. No. 4,310,440. SAPO-11, SAPO-31, SAPO-37, and SAPO-41 are described in U.S. Pat. No. 4,440,871. SM-3 is described in U.S. Pat. Nos. 4,943,424; 5,087,347; 5,158,665; and 5,208,005. MgAPSO is a MeAPSO, which is an acronym for a metal aluminumsilicophosphate molecular sieve, where the metal Me is magnesium (Mg). Suitable MgAPSO-31 catalysts include MgAPSO-31. MeAPSOs are described in U.S. Pat. No. 4,793,984, and MgAPSOs are described in U.S. Pat. No. 4,758,419. MgAPSO-31 is a preferred MgAPSO, where 31 means an MgAPSO having structure type 31. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. Nos. 4,795,623 and 4,924,027. Further catalysts and conditions for skeletal isomerization are disclosed in U.S. Pat. Nos. 5,510,306, 5,082,956, and 5,741,759.

The isomerization catalyst may also comprise a modifier selected from lanthanum, cerium, praseodymium, neodymium, samarium, gadolinium, terbium, and mixtures thereof, as described in U.S. Pat. Nos. 5,716,897 and 5,851,949. Other suitable support materials include ZSM-22, ZSM-23, and ZSM-35, which are described for use in dewaxing in U.S. Pat. No. 5,246,566 and in the article entitled "New molecular sieve process for lube dewaxing by wax isomerization," written by S. J. Miller, in Microporous Materials 2 (1994) 439-449. The teachings of U.S. Pat. Nos. 4,310,440; 4,440,871; 4,793,984; 4,758,419; 4,943,424; 5,087,347; 5,158,665; 5,208,005; 5,246,566; 5,716,897; and 5,851,949 are hereby incorporated by reference.

U.S. Pat. Nos. 5,444,032 and 5,608,968 teach a suitable bifunctional catalyst which is constituted by an amorphous silica-alumina gel and one or more metals belonging to Group VIII, and which is effective in the hydroisomerization of long-chain normal paraffins containing more than 15 carbon atoms. An activated carbon catalyst support may also be used. U.S. Pat. Nos. 5,981,419 and 5,908,134 teach a suitable bifunctional catalyst which comprises: (a) a porous crystalline material isostructural with beta-zeolite selected from boro-silicate (BOR-B) and boro-alumino-silicate (Al-BOR-B) in which the molar $SiO_2:Al_2O_3$ ratio is higher than 300:1; (b) one or more metal(s) belonging to Group VIIIA, selected from platinum and palladium, in an amount comprised within the range of from 0.05 to 5% by weight. Article V. Calemma et al., App. Catal. A: Gen., 190 (2000), 207 teaches yet another suitable catalyst.

The isomerization catalyst may be any of those well known in the art such as those described and cited above. Isomerization conditions include a temperature of about 150° C. to about 360° C. and a pressure of about 1724 kPa absolute (250 psia) to about 10342 kPa absolute (1500 psia). In another embodiment the isomerization conditions include a temperature of about 300° C. to about 360° C. and a pressure of about 3102 kPa absolute (450 psia) to about 6895 kPa absolute (1000 psia). Other operating conditions for the isomerization zone are well known in the art. Operating at low pressures allows for the optional introduction of hydrogen from another unit, such as a hydrogen plant, without the use of a make-up compressor which may be an option to reduce or eliminate hydrogen recycle. When hydrogen is not recycled, the amount of hydrogen introduced to the isomerization zone would be only slightly greater than that which is consumed, for example, an excess of about 5 to about 25 percent of the consumption requirements.

The final effluent stream, i.e., the stream obtained after all reactions have been carried out, is now processed through one or more separation steps to obtain a purified hydrocarbon stream useful as a transportation fuel. With the final effluent stream comprising both a liquid component and a gaseous component, various portions of which are to be recycled, multiple separation steps may be employed. For example, hydrogen may be first separated in an isomerization effluent separator with the separated hydrogen being removed in an overhead stream. Suitable operating conditions of the isomerization effluent separator include, for example, a temperature of 230° C. and a pressure of 4100 kPa absolute (600 psia). If there is a low concentration of carbon oxides, or the carbon oxides are removed, the hydrogen may be recycled back to the hot high pressure hydrogen stripper for use both as a stripping gas and to combine with the remainder as a bottoms stream. The remainder is passed to the isomerization reaction zone, and the hydrogen becomes a component of the isomerization reaction zone feed streams in order to provide the necessary hydrogen partial pressures for the reactor. The hydrogen is also a reactant in the deoxygenation reactors, and different feedstocks will consume different amounts of hydrogen. The isomerization effluent separator allows flexibility for the process to operate even when larger amounts of hydrogen are consumed in the first reaction zone. Furthermore, at least a portion of the remainder or bottoms stream of the isomerization effluent separator may be recycled to the isomerization reaction zone to increase the degree of isomerization.

The remainder of the final effluent after the removal of hydrogen still has liquid and gaseous components and is cooled by techniques such as air cooling or water cooling, and passed to a cold separator where the liquid component is separated from the gaseous component. Suitable operating conditions of the cold separator include, for example, a temperature of about 20 to 60° C. and a pressure of 3850 kPa absolute (560 psia). A water byproduct stream is also separated. At least a portion of the liquid component, after cooling and separating from the gaseous component, may be recycled back to the isomerization zone to increase the degree of isomerization. Prior to entering the cold separator, the remainder of the final effluent stream may be combined with the hot high pressure hydrogen stripper overhead stream, and the resulting combined stream may be introduced into the cold separator.

The liquid component contains the hydrocarbons useful as transportation fuel, termed fuel range hydrocarbons, as well as smaller amounts of naphtha and LPG. The separated liquid component may be recovered as diesel fuel, or it may be further purified in a product stripper which separates lower boiling components and dissolved gases into an LPG and naphtha stream from the jet fuel and diesel fuel products containing $C_8$ to $C_{24}$ normal and branched alkanes. Suitable operating conditions of the product stripper include a temperature of from about 20 to about 200° C. at the overhead, and a pressure from about 0 to about 1379 kPa absolute (0 to 200 psia).

The LPG and naphtha stream may be further separated in a debutanizer or depropanizer in order to separate the LPG into an overhead stream, leaving the naphtha in a bottoms stream. Suitable operating conditions of this unit include a temperature of from about 20 to about 200° C. at the overhead, and a pressure from about 0 to about 2758 kPa absolute (0 to 400 psia). The LPG may be sold as valuable product, or it may be used in other processes such as a feed to a hydrogen production facility. Similarly, the naphtha may be used in other processes, such as the feed to a hydrogen production facility, a co-feed to a reforming process, or it may be used as a fuel blending component in the gasoline blending pool, for example.

The gaseous component separated in the product separator comprises mostly hydrogen, and the carbon dioxide from the decarboxylation reaction. Other components such as carbon monoxide, propane, and hydrogen sulfide or other sulfur containing component may be present as well.

It is desirable to recycle the hydrogen to the isomerization zone, but if the carbon dioxide was not removed, its concentration would quickly build up and effect the operation of the isomerization zone. The carbon dioxide can be removed from the hydrogen by means well known in the art such as reaction with a hot carbonate solution, pressure swing absorption, etc. If desired, essentially pure carbon dioxide can be recovered by regenerating the spent absorption media.

Similarly, a sulfur containing component such as hydrogen sulfide may be present to maintain the sulfided state of the deoxygenation catalyst or to control the relative amounts of the decarboxylation reaction and the hydrogenation reaction that are both occurring in the deoxygenation zone. The amount of sulfur is generally controlled, and it can be removed before the hydrogen is recycled. The sulfur components may be removed using techniques such as absorption with an amine or by caustic wash. Of course, depending upon the technique used, the carbon dioxide and sulfur containing components, and other components, may be removed in a single separation step such as a hydrogen selective membrane.

The hydrogen remaining after the removal of at least carbon dioxide may be recycled to the reaction zone where hydrogenation primarily occurs and/or to any subsequent beds or reactors. The recycle stream may be introduced to the inlet of the reaction zone and/or to any subsequent beds or reactors. One benefit of the hydrocarbon recycle is to control the temperature rise across the individual beds. However, as discussed above, the amount of hydrocarbon recycle may be determined based upon the desired hydrogen solubility in the reaction zone which is in excess of that used for temperature control. Increasing the hydrogen solubility in the reaction mixture allows for successful operation at lower pressures, and thus reduced cost.

The following embodiment of the hydrodeoxygenation and isomerization zones is presented in illustration and is not intended as an undue limitation on the generally broad scope of the invention as set forth in the claims. The hydroprocessing and recovery process is first described in general with reference to FIG. 3. It is then described in more detail with reference to FIG. 4.

Figure 3:
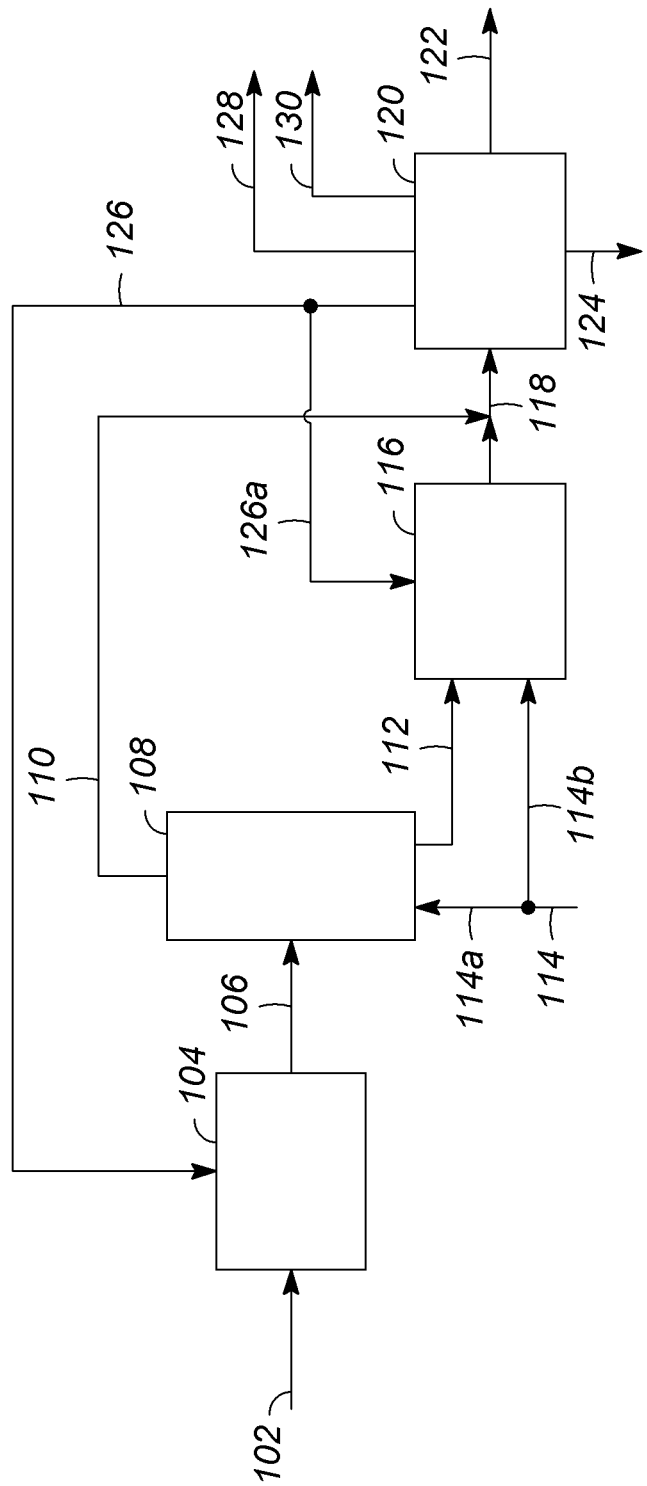
FIG. 3 is a simplified schematic of one embodiment of a hydroprocessing process.

Turning to FIG. 3, the free fatty stream substantially free of glycerol, water, and metals 102 enters deoxygenation reaction zone 104 along with recycle hydrogen 126. Deoxygenated product 106 is stripped in hot high pressure hydrogen stripper 108 using hydrogen 114a. The carbon oxides and water vapor are removed with hydrogen in overhead 110. Selectively stripped deoxygenated product 112 is passed to isomerization zone 116 along with recycle hydrogen 126a and make-up hydrogen 114b. Isomerized product 118 is combined with overhead 110 and passed to product recovery zone 120.

Carbon oxide stream 128, light ends stream 130, water byproduct stream 124, hydrogen stream 126, and branched paraffin-rich product 122 are removed from product recover zone 120. Branched paraffin-rich product 122 may be collected for use as transportation fuel, and hydrogen stream 126 is recycled to the deoxygenation reaction zone 104.

Figure 4:
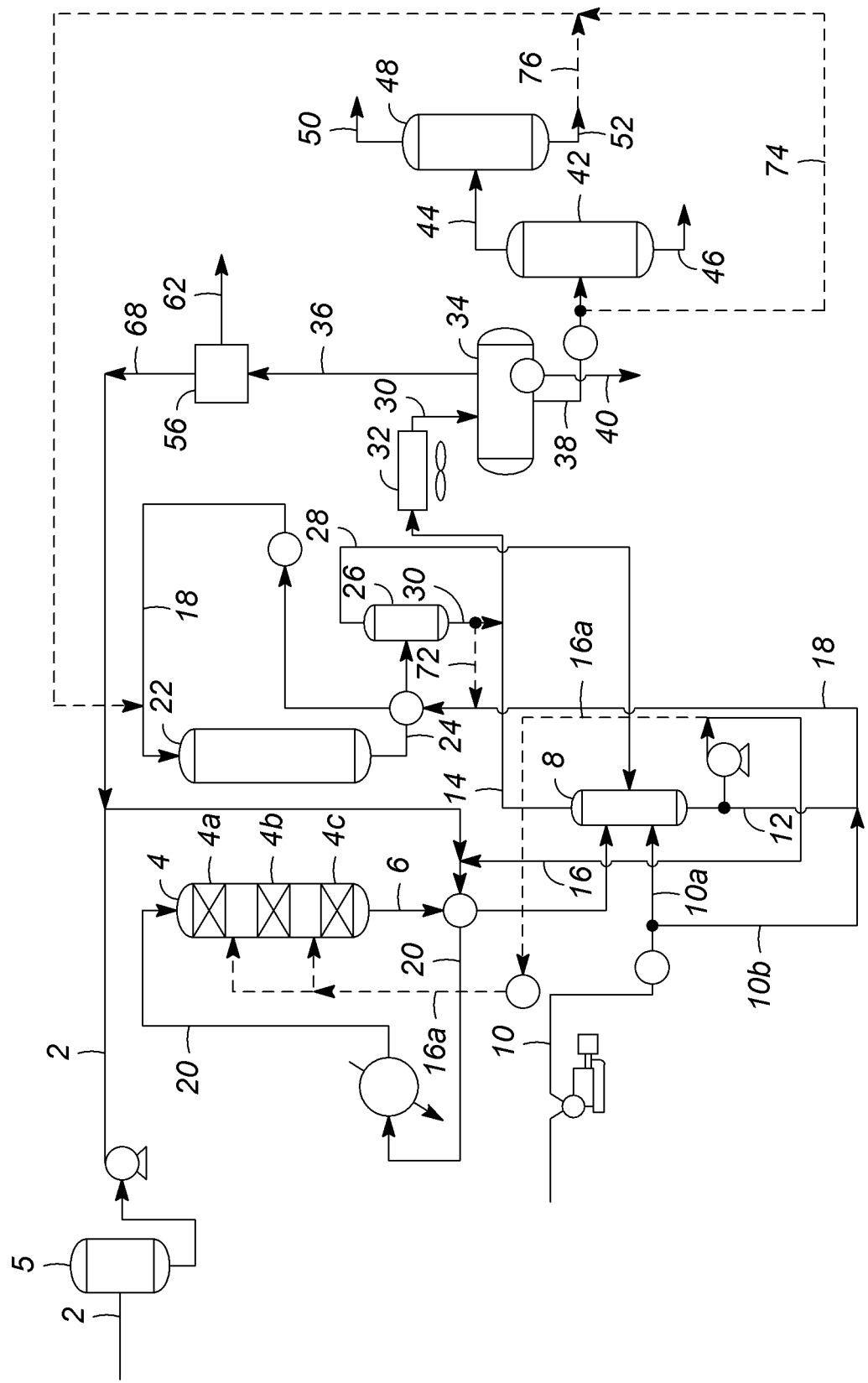
FIG. 4 is a detailed schematic of one embodiment of a hydroprocessing process.

Turning to FIG. 4, the process begins with the free fatty stream substantially free of glycerol, water, and metals 2 which may pass through an optional feed surge drum. The feedstock stream 2 is combined with recycle gas stream 68 and recycle stream 16 to form combined feed stream 20, which is heat exchanged with reactor effluent and then introduced into deoxygenation reactor 4. The heat exchange may occur before or after the recycle is combined with the feed. Deoxygenation reactor 4 may contain multiple beds shown in FIG. 4 as 4a, 4b and 4c. Deoxygenation reactor 4 contains at least one catalyst capable of catalyzing hydrodeoxygenation of the feedstock to remove oxygen. Deoxygenation reactor effluent stream 6 containing the products of the r hydrodeoxygenation reactions is removed from deoxygenation reactor 4 and heat exchanged with stream 20 containing feed to the deoxygenation reactor 4. Stream 6 comprises a liquid component containing largely normal paraffin hydrocarbons in the diesel boiling range and a gaseous component comprising hydrogen and vaporous water with minor amounts of carbon monoxide, carbon dioxide and light hydrocarbon gases.

Deoxygenation reactor effluent stream 6 is then directed to hot high pressure hydrogen stripper 8. Make up hydrogen in line 10 is divided into two portions, streams 10a and 10b. Make up hydrogen in stream 10a is also introduced to hot high pressure hydrogen stripper 8. In hot high pressure hydrogen stripper 8, the gaseous component of deoxygenation reactor effluent 6 is selectively stripped from the liquid component of deoxygenation reactor effluent 6 using make-up hydrogen 10a and recycle hydrogen 28. The dissolved gaseous component comprising hydrogen, vaporous water, carbon monoxide, and carbon dioxide is selectively separated into hot high pressure hydrogen stripper overhead stream 14. The remaining liquid component of deoxygenation reactor effluent 6 comprising primarily normal paraffins having a carbon number from about 8 to about 24 with a cetane number of about 60 to about 100 is removed as hot high pressure hydrogen stripper bottom 12.

A portion of hot high pressure hydrogen stripper bottoms forms recycle stream 16 and is combined with renewable feedstock stream 2 to create combined feed 20. Another portion of recycle stream 16, optional stream 16a, may be routed directly to deoxygenation reactor 4 and introduced at interstage locations such as between beds 4a and 4b and/or between beds 4b and 4c to aid in temperature control, for example. The remainder of hot high pressure hydrogen stripper bottoms in stream 12 is combined with hydrogen stream 10b to form combined stream 18 which is routed to isomerization reactor 22. Stream 18 may be heat exchanged with isomerization reactor effluent 24.

The product of the isomerization reactor containing a gaseous portion of hydrogen and propane and a branched-paraffin-rich liquid portion is removed in line 24, and after optional heat exchange with stream 18, is introduced into hydrogen separator 26. The overhead stream 28 from hydrogen separator 26 contains primarily hydrogen which may be recycled back to hot high pressure hydrogen stripper 8. Bottom stream 30 from hydrogen separator 26 is air cooled using air cooler 32 and introduced into product separator 34. In product separator 34, the gaseous portion of the stream comprising hydrogen, carbon monoxide, hydrogen sulfide, carbon dioxide and light hydrocarbons are removed in stream 36 while the liquid hydrocarbon portion of the stream is removed in stream 38. A water byproduct stream 40 may also be removed from product separator 34. Stream 38 is introduced to product stripper 42 where components having higher relative volatilities are separated into stream 44 with the remainder, the paraffin components, being withdrawn from product stripper 42 in line 46. Stream 44 is introduced into fractionator 48 which operates to separate butane and lighter hydrocarbons into overhead 50 leaving a naphtha bottoms 52. Any of optional lines 72, 74, or 76 may be used to recycle at least a portion of the isomerization zone effluent back to the isomerization zone to increase the amount of n-paraffins that are isomerized to branched paraffins.

The vapor stream 36 from product separator 34 contains the gaseous portion of the isomerization effluent which comprises at least hydrogen, carbon monoxide, hydrogen sulfide, and carbon dioxide and is directed to a system of amine absorbers to separate carbon dioxide and hydrogen sulfide from the vapor stream. Because of the cost of hydrogen, it is desirable to recycle the hydrogen to deoxygenation reactor 4, but it is not desirable to circulate the carbon dioxide or an excess of sulfur containing components. In order to separate sulfur containing components and carbon dioxide from the hydrogen, vapor stream 36 is passed through an amine absorber, also called a scrubber, in zone 56. The amine chosen to be employed in amine scrubber 56 is capable of selectively removing at least carbon dioxide. Suitable amines are available from DOW and from BASF, and in one embodiment the amines are a promoted or activated methyldiethanolamine (MDEA). See U.S. Pat. No. 6,337,059, hereby incorporated by reference in its entirety. Suitable amines for the first amine absorber zone from DOW include the UCARSOL™ AP series solvents such as AP802, AP804, AP806, AP810 and AP814. The carbon dioxide is absorbed by the amine, while the hydrogen passes through the amine scrubber zone and into line 68 to be recycled to the first reaction zone. The amine is regenerated, and the carbon dioxide is released and removed in line 62. Within the amine absorber zone, regenerated amine may be recycled for use again. Conditions for the first scrubber zone include a temperature in the range of 30 to 60° C. The first absorber is operated at essentially the same pressure as the reaction zone. By "essentially" it is meant that the operating pressure of the first absorber is within about 1034 kPa absolute (150 psia) of the operating pressure of the reaction zone. For example, the pressure of the absorber is no more than 1034 kPa absolute (150 psia) less than that of the reaction zone.

Example 1

A simplified comparison of the integrated hydrolysis followed by hydrodeoxygenation process with a stand alone hydrodeoxygenation process is shown in Table 1. In both cases, full conversion of feed oxygenate to water is assumed.

TABLE 1

| Hydrolysis/<br>Hydrodeoxygenation | Mass<br>Units | Hydrodeoxygenation | Mass<br>Units |
|---|---|---|---|
| C16 Triglyceride | 100.0 | C16 Triglyceride | 100.0 |
| H2O | 6.7 | | |
| Hydrolysis Products | | | |
| C16 FFA | 95.3 | | |
| Glycerol | 11.4 | | |
| | 106.7 | | |
| Hydrodeoxygenation Inputs | | | |
| C16 FFA | 95.3 | | |
| H2 | 2.2 | H2 | 3.0 |
| | 97.5 | | |
| Hydrodeoxygenation Products | | | |
| Propane | 0.0 | Propane | 5.5 |
| Diesel Range Paraffins | 84.1 | Diesel Range Paraffins | 84.1 |
| Water | 13.4 | Water | 13.4 |

Example 2

As shown in Table 2, a feedstock of brown grease with FFA to lipid weight ratio >0.3, a sulfur content over 500 wt-ppm and a metals (Na, Mg, Ca, Zn) content >1000 wt-ppm was acid-washed was reported to reduce the metals concentration below 30 wt-ppm.

TABLE 2

| Brown Grease Feedstock and Acid-Washed Product | | | | | |
|---|---|---|---|---|---|
| | S | Na | Mg | Ca | Zn |
| Brown grease as received | 640 | 37 | 61 | 1076 | 58 |
| HCl (aq) treated and washed brown grease | 428 | 4.3 | 1.5 | 13.1 | 7 |

The acid-washed brown grease could then be hydrolyzed in the presence of an acid catalyst at subcritical conditions (e.g., temperature of less than about 350° C. and a pressure of less than about 6895 kPa(g) (1000 psig)) to convert >80% of the total lipids present to FFA. Hydrolysis reaction time would be about 75 minutes.

Using the separation and purification processes described, a free fatty acid stream substantially free of glycerol, water, and metals (e.g., having less than 10 wt-ppm metals, total glycerol <0.5% by weight, and total water content <1% by weight) could be recovered from the catalytic hydrolysis reactor effluent. A glycerol-containing co-product would also be generated.

The FFA stream substantially free of glycerol, water, and metals could then be pressurized, mixed with hydrogen gas, heated, and passed over a fixed bed of hydrodeoxygenation catalyst at a reactor partial pressure of 4826 kPa (a) (700 psia) to convert more than 95% of the carbon in the free fatty acid stream substantially free of glycerol, water, and metals to oxygenate-free hydrocarbons. Catalyst and reaction conditions could be selected to minimize feedstock carbon losses to carbon oxides through decarboxylation and decarbonylation reactions.

A distillate comprising diesel fuel and jet fuel having lower heating values >40 MJ/kg could be recovered.

The glycerol-containing stream could be purified using the separation and purification processes described to a glycerol stream substantially free of free fatty acids. The glycerol stream substantially free of free fatty acids could be selectively hydrogenated in a hydrogenation zone under hydrogenation conditions (e.g., a temperature of about 190° C. and a pressure of about 8274 kPa (g) (1200 psig) in the presence of a hydrogenation catalyst and a small amount of alkali (e.g., 1% NaOH). The process could achieve about 90% conversion of glycerol, with about 91% selectivity to propylene glycol and 3% selectivity to ethylene glycol.

Example 3

A feedstock of marine algae (nanochloropsis) with a dry basis neutral lipid content of 20% and a polar lipid content of 10% could be pretreated with an aqueous acid stream to remove at least a portion of the metals and cellulosic materials.

A lipid-enriched fraction would be recovered and then hydrolyzed in the presence of an acid catalyst at subcritical conditions to convert 98% of the neutral lipids and >50% of the polar lipids present to FFA. Hydrolysis reaction time would be about 90 minutes.

Using the separation and purification processes described, a free fatty acid stream substantially free of glycerol, water, and metals, (e.g., having less than 10 wt-ppm metals, total glycerol <0.5% by weight, and total water content <1% by weight) could be recovered from the catalytic hydrolysis reactor effluent, and a glycerol stream comprising, for example, <5% wt of the total fatty acids present in the glyceride containing stream.

The free fatty acid stream substantially free of glycerol, water, and metals would then be pressurized, mixed with hydrogen gas, heated, and passed over a fixed bed of hydrodeoxygenation catalyst at a reactor partial pressure of 5516 kPa (a) (800 psia) to convert more than 90% of the carbon in the free fatty acid stream substantially free of glycerol, water, and metals to oxygenate-free hydrocarbons. Catalyst and reaction conditions could be selected to minimize feedstock carbon losses to carbon oxides through decarboxylation and decarbonylation reactions.

A distillate comprising diesel fuel and jet fuel having lower heating values >40 MJ/kg could be recovered.

The glycerol-containing stream could be purified using the separation and purification processes described to a glycerol stream substantially free of free fatty acids. The glycerol stream substantially free of free fatty acids could be selectively hydrogenated in a hydrogenation zone under hydrogenation conditions (e.g., a temperature of about 190° C. and a pressure of about 8274 kPa (g) (1200 psig) in the presence of a hydrogenation catalyst and a small amount of alkali (e.g., 1% NaOH). The process could achieve about 90% conversion of glycerol, with about 91% selectivity to propylene glycol and 3% selectivity to ethylene glycol.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An integrated process for producing paraffins and polyols from a glyceride containing renewable feedstock comprising:
   reacting the glyceride containing renewable feedstock with water in a first reaction zone to produce an effluent stream comprising free fatty acids, glycerol, and water;
   separating the free fatty acids from the glycerol and water to produce a free fatty acid stream substantially free of glycerol, water, and metals, and a glycerol stream substantially free of free fatty acids;
   reacting the free fatty acid stream substantially free of glycerol, water, and metals with hydrogen from a hydrogen source in a second reaction zone in the presence of a hydroprocessing catalyst under hydroprocessing conditions thereby hydrodeoxygenating the free fatty acid stream substantially free of glycerol, water, and metals to produce a reaction product comprising n-paraffins and water;
   recovering the n-paraffin reaction product;
   reacting the glycerol stream substantially free of free fatty acids with hydrogen from the hydrogen source in a third reaction zone under selective hydrogenation conditions to produce a reaction product comprising polyols;
   recovering the polyol reaction product.

2. The integrated process of claim 1 further comprising contacting at least a portion of the n-paraffin reaction product with an isomerization catalyst under isomerization conditions to isomerize at least a portion of the n-paraffins to isoparaffins.

3. The process of claim 1 wherein separating the free fatty acids from the glycerol and water comprises at least one of hot depressurization, cyclonic vapor liquid separation, liquid-liquid separation, multi-effect evaporation, steam distillation, vacuum distillation, reactive distillation, liquid extraction, adsorption, filtration, membrane separation, absorption, or ion exchange.

4. The integrated process of claim 1 wherein separating the free fatty acids from the glycerol and water comprises:
   separating the effluent stream into a free fatty acid enriched stream and a glycerol containing stream;
   purifying the free fatty acid enriched stream to form the free fatty acid stream substantially free of glycerol, water, and metals.

5. The integrated process of claim 4 further comprising purifying the glycerol containing stream to form the glycerol stream substantially free of free fatty acids.

6. The process of claim 1 wherein the free fatty acid stream substantially free of glycerol, water, and metals has less than about 5 wt % glycerol, less than about 5 wt % water, and less than about 20 ppm (wt) metals.

7. The process of claim 1 wherein reacting the glyceride containing renewable feedstock with water takes place in the presence of a hydrolysis catalyst.

8. The process of claim 1 wherein reacting the glyceride containing renewable feedstock with water is performed at sub-critical conditions.

9. The process of claim 1 wherein reacting the glyceride containing renewable feedstock with water takes place at a pressure of less than about 5516 kPa(g) and a temperature of less than about 300° C.

10. The process of claim 1 wherein the glyceride containing renewable feedstock comprises algae or a stream derived from algae.

11. The process of claim 1 further comprising contacting the glyceride containing renewable feedstock with one or more of an acid, a base, an extractive material, or an adsorptive material to remove contaminants from the glyceride containing renewable feedstock before reacting the glyceride containing renewable feedstock with the water.

12. The process of claim 1 wherein the hydroprocessing conditions include a temperature of less than about 400° C., a hydrogen partial pressure of greater than about 3450 kPa, an $H_2$ to organic oxygen ratio greater than about 5, and in the presence of a base metal catalyst.

13. The process of claim 1 wherein at least about 80 wt % of the total lipids in the glyceride containing renewable feedstock are converted to free fatty acids in the reaction with water.

14. The process of claim 1 wherein when reacting the glyceride containing renewable feedstock with water, a ratio of water to total lipids in the first reaction zone is greater than a stoichiometric minimum required for complete hydrolysis.

15. The process of claim 1 wherein at least about 80 wt % of oxygen in the free fatty acid stream substantially free of glycerol, water, and metals is converted to water and less than 10% of carbon in the free fatty acid stream substantially free of glycerol, water, and metals is reacted to form CO or $CO_2$ in the second reaction zone.

16. The process of claim 1 wherein at least about 80% of the n-paraffins in the reaction product have an even number of carbon atoms.

17. The process of claim 1 wherein reacting the free fatty acid stream substantially free of glycerol, water, and metals with hydrogen comprises selective catalytic hydrodeoxygenation.

18. An integrated process for producing paraffins and propylene glycol from a glyceride containing renewable feedstock comprising:
    reacting the glyceride containing renewable feedstock with water in a first reaction zone to produce an effluent stream comprising free fatty acids, glycerol, and water;
    separating the effluent stream into a free fatty enriched stream and a glycerol containing stream;
    purifying the free fatty acid enriched stream to form a free fatty acid stream substantially free from glycerol, water, and metals;
    purifying the glycerol enriched stream to form a glycerol stream substantially free of free fatty acids;
    reacting the free fatty acid stream substantially free of glycerol, water, and metals with hydrogen from a hydrogen source in a second reaction zone in the presence of a hydroprocessing catalyst under hydroprocessing conditions thereby hydrodeoxygenating the free fatty acid stream substantially free of glycerol, water, and metals to produce a reaction product comprising n-paraffins and water;
    recovering the n-paraffin reaction product;
    reacting the glycerol stream substantially free of free fatty acids with hydrogen from the hydrogen source in a third reaction zone under selective hydrogenation conditions to produce a reaction product comprising propylene glycol;
    recovering the propylene glycol reaction product.

19. The process of claim 18 wherein the free fatty acid stream substantially free of glycerol, water, and metals has less than about 5 wt % glycerol, less than about 5 wt % water, and less than about 20 ppm (wt) metals.

20. The process of claim 18 wherein at least about 80% of the total lipids in the triglyceride-rich renewable feedstock are converted to free fatty acids in the reaction with water and wherein less than 10% of carbon in the free fatty acid stream substantially free of glycerol, water, and metals is reacted to form CO or $CO_2$ in the second reaction zone.

* * * * *